United States Patent [19]

Dudasik et al.

[11] Patent Number: 5,358,534
[45] Date of Patent: Oct. 25, 1994

[54] FEMORAL COMPONENT FOR A HIP PROSTHESIS

[75] Inventors: Michael W. Dudasik, Nutley, N.J.; Anthony K. Hedley, Paradise Valley, Ariz.; David S. Hungerford, Cockeysville, Md.; Matthew P. Poggie, Union City, N.J.

[73] Assignee: Howmedica Inc., New York, N.Y.

[21] Appl. No.: 55,426

[22] Filed: Apr. 29, 1993

[51] Int. Cl.⁵ .............................................. A61F 2/32
[52] U.S. Cl. ............................................... 623/22
[58] Field of Search .................... 623/16, 18, 22, 23

[56] References Cited

U.S. PATENT DOCUMENTS

| | | | |
|---|---|---|---|
| 4,435,854 | 3/1984 | Keller | 623/23 |
| 4,589,883 | 5/1986 | Kerra | 623/22 |
| 4,752,296 | 6/1988 | Buechel et al. | 623/23 |
| 4,813,963 | 3/1989 | Hori et al. | 623/23 |
| 4,979,958 | 12/1990 | Niwa et al. | 623/23 |
| 5,002,580 | 3/1991 | Noble et al. | 623/18 X |
| 5,041,141 | 8/1991 | Ypna et al. | 623/23 |
| 5,181,930 | 1/1993 | Dunbleton et al. | 623/23 |

FOREIGN PATENT DOCUMENTS 2551013  5/1976  Fed. Rep. of Germany ........ 623/23

Primary Examiner—Randall L. Green
Assistant Examiner—Mary Beth Jones
Attorney, Agent, or Firm—Peter C. Richardson; Lawrence C. Akers; Raymond W. Augustin

[57] ABSTRACT

A femoral component for a hip prosthesis has a distal portion defining a central longitudinal axis. The component has a generally conically shaped mid-shaft portion and a proximal portion with a shape based on the reamer and a shaped chisel used by the surgeon to prepare the proximal metaphysis and medullary canal. The proximal portion is shaped in a manner wherein a cross-section taken perpendicular to the central axis has a medial side formed as a first circular arc, a corner of the cross-section formed by the posterior and lateral sides as a second circular arc with a center on the central axis. The posterior side is arcuate and concave and tangent to the first and second circular arcs, with the anterior side being arcuate and convex.

8 Claims, 5 Drawing Sheets

FEMORAL COMPONENT FOR A HIP PROSTHESIS

BACKGROUND OF THE INVENTION

1. Field of the Invention

The present invention relates to a femoral component for a hip prosthesis to be used in total hip arthroplasty. More specifically, it relates to a femoral component having a shape which provides a better fit with the femoral medullary canal.

2. Description of the Prior Art

It is possible to eliminate severe pain in hip joints as a result of arthritis or other infirmities by implanting a stem within a femoral intramedullary canal. A ball on the proximal end of the stem cooperates with a prosthetic socket implanted in a prepared natural acetabulum and thereby provides for articulation between the femur and the acetabulum after the femoral head has been resected and the proximal femur cleared of cancellous bone proximally and fatty tissue distally.

In order to maintain pain-free articulation of the hip joint following prosthesis implantation, it is essential that fixation be attained between the stem and healthy bone bed. Such a fastening is accomplished by several methods. A polymethylmethacrylate cement can act as a bone between the implant and the interstices of the prepared bone bed. A second method known as press fit relies on the dimensional difference between the implant and prepared bone bed for stability. A third fixation method provides a 3-dimensional texture on the implant's surface that, when used in a "line to line" or slightly undersized prepared bone bed, allows for bony ingrowth texture.

Various patents relate to a femoral component for press fit with and biological fixation to the wall of the proximal metaphysis and intramedullary canal. For example, U.S. Pat. No. 4,589,883 teaches a proximal portion which is elliptical in cross-section with its major and minor axes twisted along the proximal direction. U.S. Pat. No. 4,435,854 (now Reissue Patent 32,471) relates to a hip joint prosthesis having a stem which, in its proximal region, has a curvature in the anterior-posterior plane with a center of curvature anteriorly and, in its distal region, includes a shank having a curvature in the opposite direction in the anterior-posterior plane, i.e. at its center of curvature posteriorly. This design supposedly reduces the tendency of the shank to turn within the medullary canal.

U.S. Pat. No. 5,002,580 relates to a femoral component designed to provide a non-uniform interference press fit with the intramedullary canal. With this design, the femoral canal is prepared in such a manner that the prosthesis has line-to-line contact with cortical bone on the lateral side and produces an interference fit with the softer cancellous bone on the medial side of the femur. U.S. Pat. No. 4,813,963 relates to a femoral component for a hip prosthesis including a proximal portion with an asymmetric contour defining an anterior side which forms an acute angle with a lateral side and the posterior side approaches the anterior side in a direction of the medial side. Furthermore, the medial side is arcuate in shape while the other sides include linear edges in cross-section.

While the prior art femoral components have provided a stem and surgical techniques which produced acceptable results, improved stem fit and a simplified surgical procedure are still desirable.

In addition to varying proximal geometries, a femoral prosthesis can be broadly characterized as also having straight or curved stems. Straight prostheses are left/-right interchangeable and are less technically demanding to implant than curved stem prostheses. On the other hand, curved stem prostheses, while being somewhat more demanding for the surgeon to implant, provide the advantage of an improved fit within the prepared femoral canal. The design of the present invention possesses a unique geometry which provides the superior proximal fit afforded by a curved stem prosthesis, but can utilize the proven canal preparation techniques employed in the implantation of straight stem prostheses. The prostheses of the present invention can be broken into three regions and can be described geometrically as a distal parabolic section, a conical mid-stem section and a proximal geometry which medially and anteriorly conforms to the anatomy of a natural femoral medullary canal, and posteriorly and laterally fills the space created by a guided chisel used to groove the trochanteric bed.

The improved proximal fit is accomplished in the present invention by having a direct relationship between the prosthesis shape and the shape of the instruments used to prepare the femur. This relationship uses known mathematical techniques to generate surfaces of the proximal prosthesis from the chisel profile and sectional radii of the reamer. This allows the surgeon to prepare the proximal femur knowing that he will have excellent proximal fit, especially posteriorly and laterally.

SUMMARY OF THE INVENTION

It is an object of the invention to provide a femoral component for use in total hip arthroplasty having a shape which allows for a tight fit within the prepared proximal femur.

It is yet another object of the invention to provide a femoral component shaped so that it may be implanted within a femoral canal with simple, accurate preparation by the surgeon, producing an excellent fit therein.

These and other objects of the invention are achieved by a femoral component for a hip prosthesis which has a distal portion defining a central longitudinal axis. The femoral component has a proximal portion shaped in a manner wherein a cross-section taken perpendicular to the central axis has a medial, posterior, lateral and anterior side. The medial side is formed as a first circular arc having a center located within the cross-section. The corner of the cross-section formed by the posterior and lateral sides is formed as a second circular arc with a center on the central axis. The anterior side is substantially arcuate and convex in form and is tangent to the first circular arc at the point of intersection therewith. The posterior side is also substantially arcuate, but concave in form and is tangent to both the first and second circular arcs. A generally arcuate portion connects the second circular arc with the anterior side, the connection being made at connecting points on the second circular arc and the anterior side such that the arcuate portion forms a tangent with the second circular arc and the anterior side at the connection point.

The substantially arcuate anterior side of each cross-section of the proximal portion is an arc of a circle having its center on a line extending through the center of said second circular arc, which line is also perpendicular to a line containing the central axis on both the centers of said first and second circular arcs. The radii of the arcs is related to the radii of the reamer which will be used by the surgeon to prepare the canal.

The substantially arcuate posterior surface of each cross-section is an arc of a circle having its center on a line extending through the center of the first circular arc and perpendicular to the plane containing the central axis and the centers of the first and second circular arcs. In the anterior to posterior view, the lateral side of the femoral component in the proximal area diverges away from the central axis on moving from proximal to distal parallel to the central axis.

These and other objects and advantages of the present invention will become apparent from the following description of the accompanying drawings, which disclose one embodiment of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views:

FIG. 4a is a cross-sectional view of the hip stem of FIG. 1 along lines 4a—4a;

DESCRIPTION OF THE PREFERRED EMBODIMENT

Figure 1:
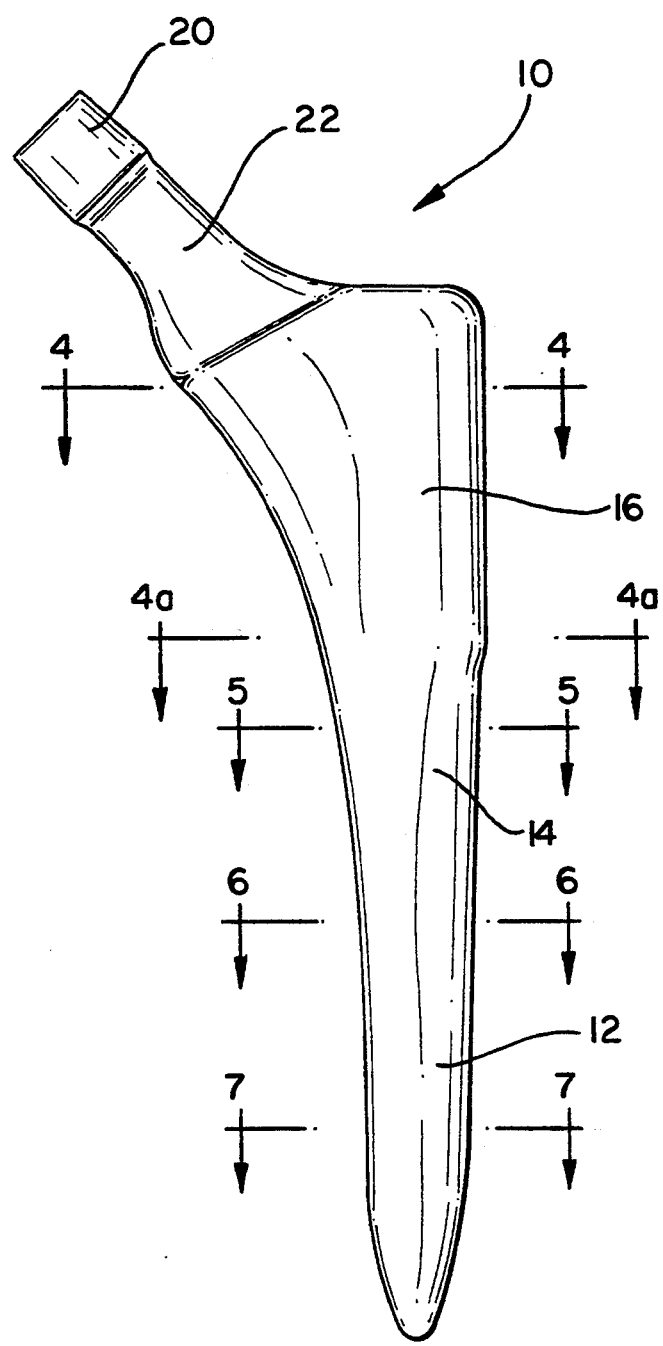
FIG. 1 is an elevation view of the hip stem of the present invention along the anterior-posterior plane.
Figure 2:
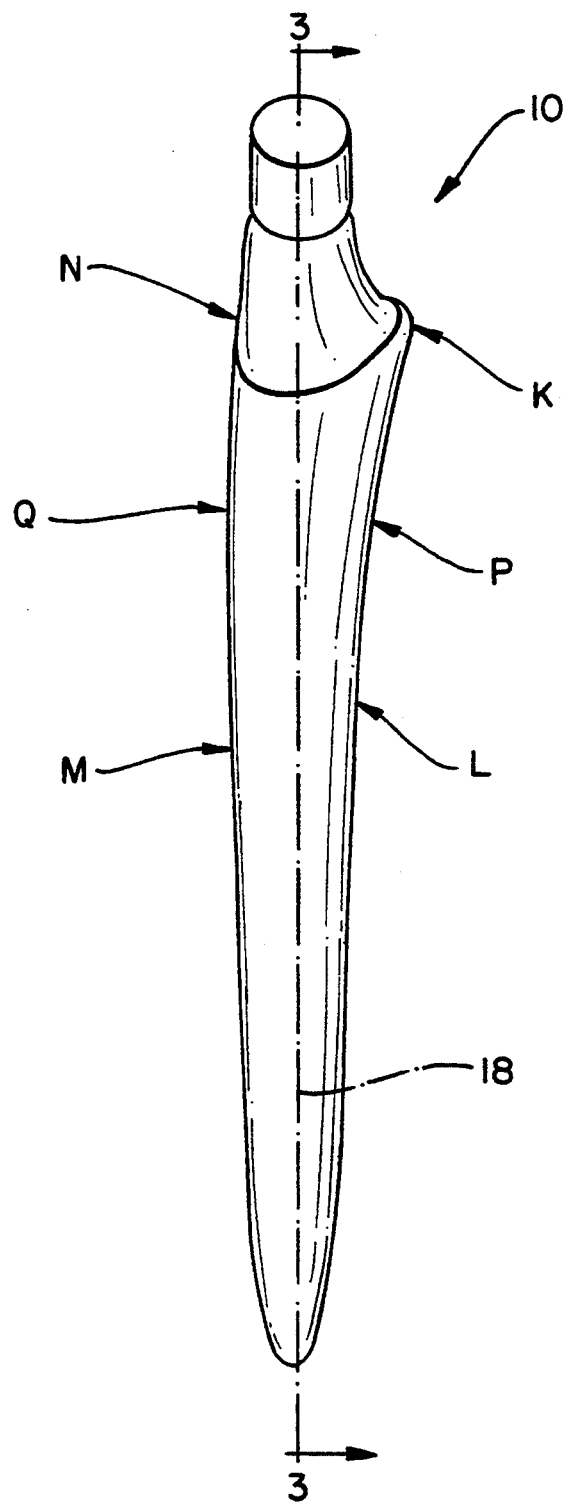
FIG. 2 is an elevation view of the hip stem of the present invention along the medial-lateral plane.
Figure 3:
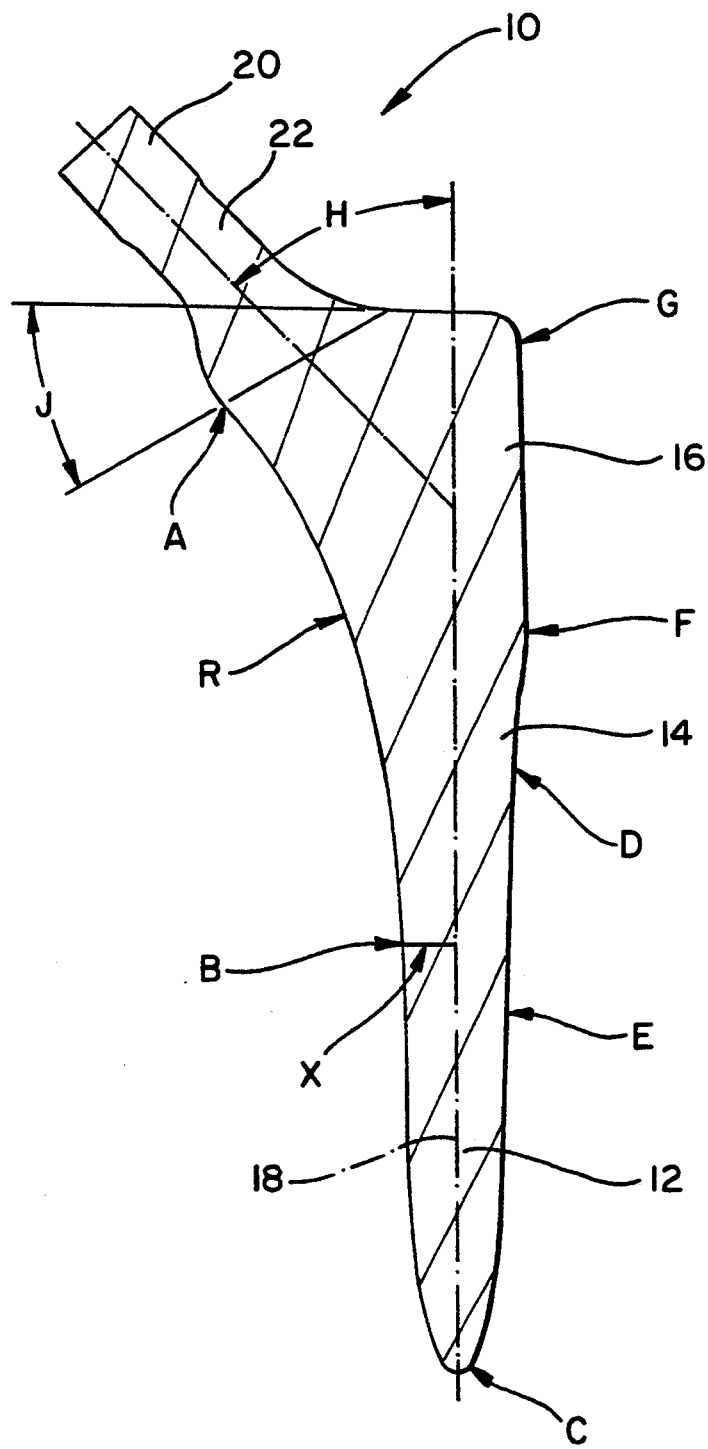
FIG. 3 is a cross-sectional view of the hip stem of the present invention along lines 3—3 of FIG. 2.

Referring to FIGS. 1-3 there is shown the femoral component of the present invention generally denoted as 10. The prosthesis 10 can be broken into a distal region 12, a mid-stem region 14 and a proximal region 16. Distal region 12 can be described geometrically as distal parabolic section, mid-stem region 14 and the proximal generally conical region 16 conform medially and anteriorly to the anatomy, and posteriorly and laterally fills the space created by a shaped chisel (not shown).

Referring to FIGS. 2 and 3, a central axis 18 extends through prosthesis 10 and generally coincides with the axis of the proximal femur. Prosthesis 10 is provided with lateral flare F at the juncture of the proximal portion 16 and section 14, allowing for additional stress transfer to the cortex in this region. In the preferred embodiment distal section 12 is formed as a parabola. The intent of this shape is to afford excellent fit in a large range of femurs, most notably in the anterior-posterior dimension and also improves the stress transfer to the bone pedestal often formed in this region.

Figure 8:
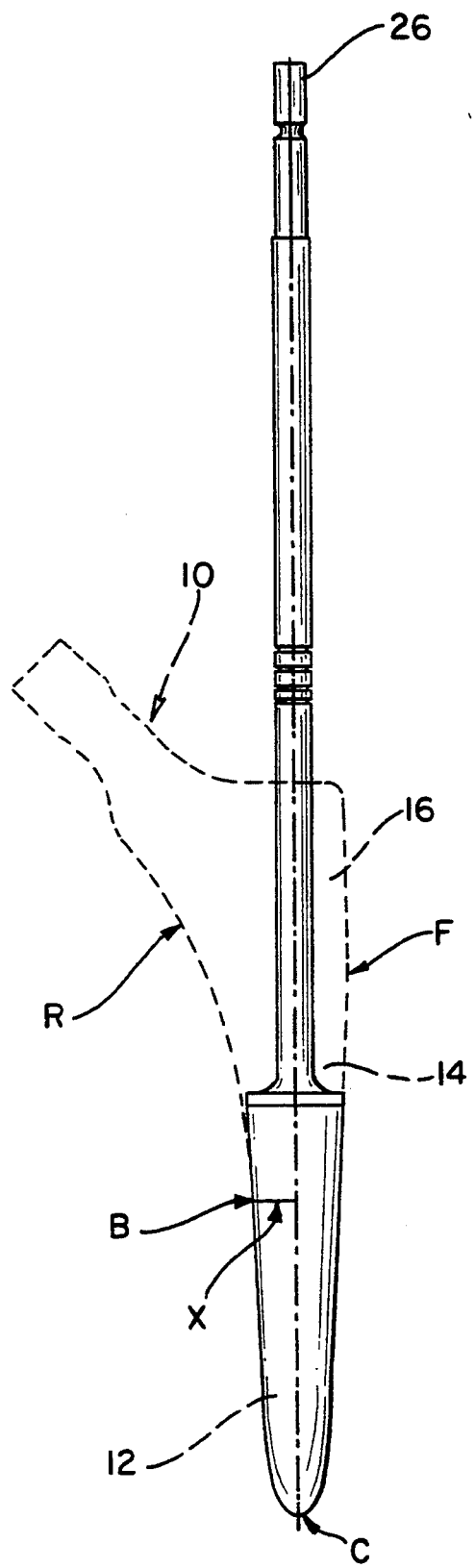
FIG. 8 is an elevation view of a reamer along a medial-lateral plane with the femoral component of the present invention in phantom.
Figure 9:
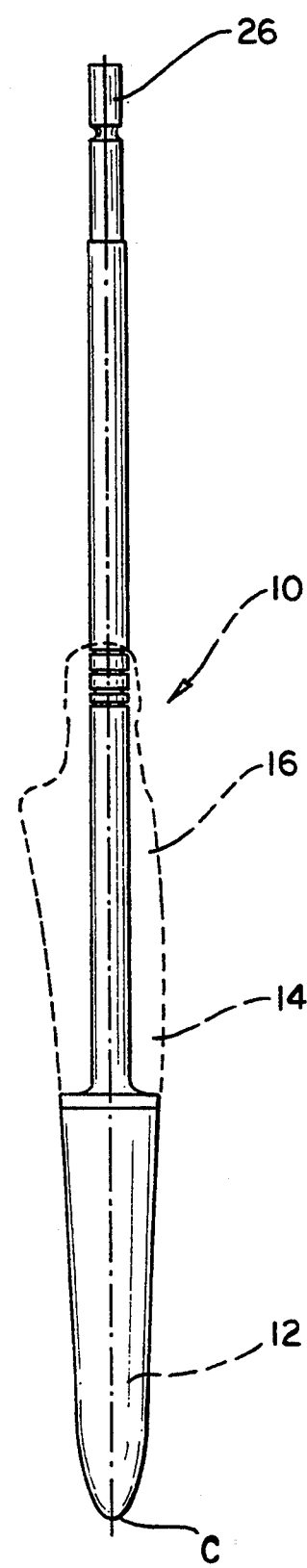
FIG. 9 is an elevation view of the reamer of FIG. 8 along an anterior-posterior plane.

A rigid reamer of predetermined shape may be used to shape the canal. Such reamers matching the distal and midshaft stem shape are shown in FIGS. 8 and 9. The reamer profile generally mimics the entire distal and midshaft shape of the femur canal, based on cadaveric studies. Reamers are currently available and presently used in medullary canal preparation such as that shown in Howmedica Inc. 1993 Catalog as part number 6059-0-510, however, these reamers are not based on the entire size and shape of the medullary canal based on studies of typical femurs. The reamer of the present invention is shaped to match approximately the lateral half of the proximal face of the implant in the area of the greater trochanter. This allows for an opening in which to more easily introduce a broach (not shown) which is used to shape the proximal femur.

Referring to FIG. 3, a medial curvature R is defined between points A and B, meeting the reamer shape at point B. As shown in FIGS. 8 and 9, the reamer 26 is shaped to coincide with the distal/midshaft implant shape from point B to the parabolic tip C, and laterally to point D. The parabola extends 3 cm, at which point it is blended into a conic of radius E.

The basic shape of the stem and reamer were derived from a cadaveric study in which a population of femurs were x-rayed and sectioned and the dimensions of proximal metaphysis and the medullary canal were measured and entered into a computer data base. Several reamer shapes were developed for bone groups of similar dimensions. Further iterative fitting of each group generated an average stem shape for approximately the proximal two thirds of the stem. The geometric relationships of the proximal stem cross-sections of the present invention were developed from the these studies and closely match the recorded cadaveric data. In the preferred system a kit is provided with approximately ten reamers and ten matching stems which correspond to ten size groups which cover the vast majority of all the femurs in the population of hips surveyed. The distal portion 12 of each stem in the kit is shaped like the corresponding reamer and thus is in the form of a paraboloid having a central axis corresponding to the measured central axis. The paraboloid forms a pointed distal tip.

In the preferred embodiment the proximal lateral face of component 10 is defined as line F-G and diverges outwardly from axis 18. This allows for greater femur to implant contact laterally when compared to the medial-lateral dimension of the osteotomy window. Between points D and F a transitional flare occurs, blending the proximal geometry to the distal reamer shape. The preferred trunnion 20 and neck 22 make an angle H of approximately 45° to the axis 18. The trunnion allows for attachment of modular femoral heads of differing diameters and offsets. The neck is enlarged at point A providing a pseudo collar to resist subsidence.

In a preferred surgical procedure, the osteotomy is made at an angle J of 30° from a perpendicular to the axis 18. This angle retains calcar bone stock, thereby enhancing rotational stability and stress transfer. Neck strength is also improved over a similar 45° osteotomy as the length of neck 22 is effectively shorter.

The shape of prosthesis 10 shown in the figures is the same as the shape of the reamer used to prepare the distal canal, being identical from point L anteriorly and around the distal tip to point M posteriorly. Analysis of femurs through planar x-ray films and 3-D computer representations has defined the proximal anterior radius P between points K and L for several implant sizes. The analysis also dictates proximal posterior radius Q, between points N and M, blending the reamer shape into the posterior aspect area. Note that radii P and Q necessitate left and right (i.e. anatomic)implants.

Figure 4:
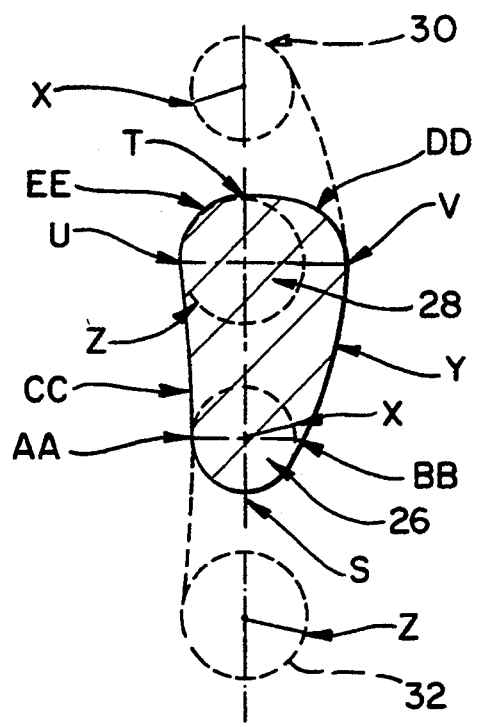
FIG. 4 is a cross-sectional view of the hip stem of FIG. 1 along lines 4—4.

Referring to FIG. 4 the cross-section is defined as a transverse cut at the medial aspect of the osteotomy, perpendicular to axis 18. Points S, T, U and V are defined as the points where the A-P and M-L profiles (FIGS. 2 and 3) bisect the plane of FIG. 4. Lines S-T and U-V are at 90° to one another. This angle does not change throughout proximal portion 16. A radius X is defined at point B, where the medial curvature R intersects the distal reamer shape. Radius X also exists at the identical location on the reamer. Radius X is constant proximal to point B, and has its center point directly lateral to point S. The anterior radius Y is defined as an arc tangent to circle 26 of radius X, through point V and tangent to a second circle 30 of radius X, mirrored through line U-V. A circle 28 of radius Z is placed at the intersection of lines S-T and U-V. The value of radius Z is that of the distance between point U and line S-T. This radius is mirrored in a circle 32 through line AA-BB, which is parallel to line U-V and through the center of circle 26.

Figure 4A:
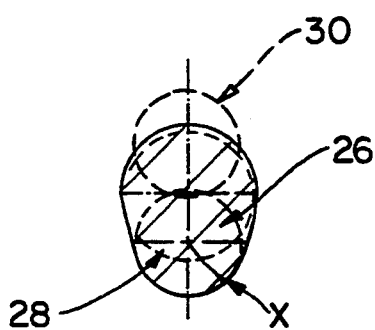
Figure 5:
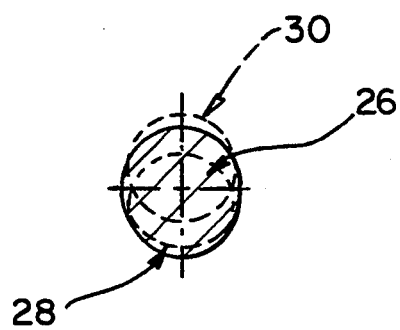
FIG. 5 is a cross-sectional view of the hip stem of FIG. 1 along lines 5—5.

The lateral shape of FIG. 4 is formed by polynomial splines DD and EE. Splines represent arcs of constantly changing radius defined in 2 or 3 dimensional space. Spline generation is available in several computer aided design (CAD) systems. These splines or arcs blend smoothly into radii Y and Z respectively. The splines also have zero slope at point T, i.e. they are parallel to line U-V. Posterior radius CC is now constructed similar to radius Y using circles 28 and 32, and point AA. Note that radius Y is convex and radius CC is concave. The concavity allows for preservation of the proximal femur's posterior cortex. In viewing the implant down axis 18, FIG. 4 can be seen to blend into the reamer shape; this occurs at point E for splines DD and EE, and point B for radii X, Y, Z and CC. FIGS. 4A and 5 show this transition. Note the decrease in lengths of lines S-T and U-V, the decrease in the center to center dimension of circles 26 and 30, and the increased lateral conformity of the sections to circle 28. The transition to a circular section is essentially complete at FIG. 6. A section identical in location on the reamer produces a like size view. FIG. 7 describes a diameter smaller than and arranged coaxially to FIG. 6.

Figure 6:
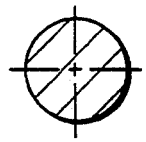
FIG. 6 is a cross-sectional view of the hip stem of FIG. 1 along lines 6—6.
Figure 7:
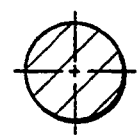
FIG. 7 is a cross-sectional view of the hip stem of FIG. 1 along lines 7—7.

FIGS. 6 and 7 are cross-sections through the distal stem region 12. Since this region is parabolic in shape, the cross-sections are generally circular.

While one example of the present invention has been described, it is obvious that many changes and modifications may be made thereunto, without departing from the spirit and scope of the invention.

We claim:

1. A femoral component for a hip prosthesis comprising:
    a distal portion defining a central longitudinal axis of the component for disposition within an intramedullary canal of a femur; and
    a proximal portion having a cross-section perpendicular to the central axis defining medial, posterior, lateral and anterior surfaces, said medial surface formed as a first circular arc having a center located within said cross-section, a corner of said cross-section formed by said posterior and said lateral surfaces formed as a second circular arc with a center on said central axis, said anterior surface being substantially arcuate and convex in form and being tangent to said first circular arc at the point of intersection therewith, said posterior surface being substantially arcuate and concave in form and being tangent to both said first and second circular arcs and a generally arcuate portion connecting said second circular arc and said anterior surface, the connection being made at a connecting point on said second circular arc and said anterior surface and said arcuate portion forming a tangent therewith at said connecting points.

2. The femoral component as set forth in claim 1 wherein a lateral side of said femoral component formed by said lateral surface of said cross-section diverges away from said central axis when moving distally therealong.

3. The femoral component as set forth in claim 1 wherein said substantially arcuate anterior surface is an arc of a circle having its center on a plane through said central axis and perpendicular to a plane containing said central axis and both said centers of said first and second circular arcs.

4. The femoral component as set forth in claim 3 wherein said substantially arcuate posterior surface is an arc of a circle having its center on a plane extending through the center of said first circular arc and perpendicular to said plane containing said central axis and both said centers of said first and second circular arcs.

5. The femoral component as set forth in claim 1 wherein said distal portion stem is having an outer surface in the form of a surface of revolution generated by rotating a parabolic cross-section about said central longitudinal axis.

6. The femoral component as set forth in claim 5 further including a midstem region having a generally conically shaped outer surface extending from said distal portion to said proximal portion.

7. A femoral component for a hip prosthesis comprising:
    a distal portion defining a central longitudinal axis of the component for disposition within an intramedullary canal of a femur; and
    a proximal portion shaped in a manner wherein a cross-section taken perpendicular to the central axis has a medial, posterior, lateral and anterior side, said medial side formed as a first circular arc having a center located within said cross-section, a corner of said cross-section formed by said posterior and said lateral sides formed as a second circular arc with a center on said central axis, said anterior side being substantially arcuate and convex in form and being tangent to said first circular arc at the point of intersection therewith, said posterior side being substantially arcuate and concave in form and being tangent to both said first and second circular arcs and a generally arcuate portion connecting said second circular arc and said anterior side, the connection being made at connecting points on said second circular arc and said anterior side with said arcuate portion forming a tangent, said second circular arc and said anterior side at said connecting points.

8. The femoral component as set forth in claim 7 wherein said substantially arcuate anterior side is an arc of a circle having its center on a line extending through the center of said second circular arc and perpendicular to a line through said central axis and both said centers of said first and second circular arcs.

* * * * *